(12) United States Patent
Chen et al.

(10) Patent No.: US 12,048,313 B2
(45) Date of Patent: *Jul. 30, 2024

(54) COMBINATION OF 25-HYDROXYVITAMIN D AND ANTIOXIDANTS/ANTI-INFLAMMATORIES FOR POULTRY OVARIAN HEALTH

(71) Applicant: DSM IP ASSETS B.V., Heerlen (NL)

(72) Inventors: Shuen Ei Chen, Kaiseraugst (CH); Thau Kiong Chung, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/703,955

(22) Filed: Mar. 24, 2022

(65) Prior Publication Data

US 2022/0211077 A1 Jul. 7, 2022

Related U.S. Application Data

(63) Continuation of application No. 15/542,091, filed as application No. PCT/EP2016/050749 on Jan. 15, 2016, now abandoned.

(Continued)

(30) Foreign Application Priority Data

May 8, 2015 (EP) .................................. 15166937

(51) Int. Cl.
| | |
|---|---|
| *A23K 20/174* | (2016.01) |
| *A23K 20/179* | (2016.01) |
| *A23K 20/20* | (2016.01) |
| *A23K 50/10* | (2016.01) |
| *A23K 50/42* | (2016.01) |
| *A23K 50/48* | (2016.01) |
| *A23K 50/75* | (2016.01) |
| *A61K 9/00* | (2006.01) |
| *A61K 31/015* | (2006.01) |
| *A61K 31/122* | (2006.01) |
| *A61K 31/197* | (2006.01) |
| *A61K 31/355* | (2006.01) |
| *A61K 31/375* | (2006.01) |
| *A61K 31/4188* | (2006.01) |
| *A61K 31/455* | (2006.01) |
| *A61K 31/519* | (2006.01) |
| *A61K 31/525* | (2006.01) |
| *A61K 31/593* | (2006.01) |

(Continued)

(52) U.S. Cl.
CPC .......... *A23K 20/174* (2016.05); *A23K 20/179* (2016.05); *A23K 20/30* (2016.05); *A23K 50/10* (2016.05); *A23K 50/42* (2016.05); *A23K 50/48* (2016.05); *A23K 50/75* (2016.05); *A61K 9/0056* (2013.01); *A61K 31/015* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/455* (2013.01); *A61K 31/519* (2013.01); *A61K 31/525* (2013.01); *A61K 31/593* (2013.01); *A61K 31/675* (2013.01); *A61K 33/04* (2013.01); *A61K 33/26* (2013.01); *A61K 33/32* (2013.01); *A61K 33/34* (2013.01); *A61P 3/06* (2018.01); *A61P 3/08* (2018.01); *A61P 9/00* (2018.01); *A61P 15/00* (2018.01); *A61P 15/08* (2018.01); *A61P 39/00* (2018.01)

(58) Field of Classification Search
CPC .... A23K 20/174; A23K 20/179; A23K 20/30; A23K 50/10; A23K 50/42; A23K 50/48; A23K 50/75; A61K 9/0056; A61K 31/015; A61K 31/122; A61K 31/197; A61K 31/355; A61K 31/375; A61K 31/4188; A61K 31/455; A61K 31/519; A61K 31/525; A61K 31/593; A61K 31/675; A61K 33/04; A61K 33/26; A61K 33/32; A61K 33/34; A61P 3/06; A61P 3/08; A61P 9/00; A61P 15/00; A61P 15/08; A61P 39/00; A61P 50/40; Y10S 426/807

See application file for complete search history.

(56) References Cited

U.S. PATENT DOCUMENTS

| 6,034,075 A | 3/2000 | Thys-Jacobs | |
| 2003/0125229 A1* | 7/2003 | Rodriguez | ............. A61K 31/56 514/182 |

(Continued)

FOREIGN PATENT DOCUMENTS

| CN | 1615139 | 5/2005 |
| CN | 1720030 | 1/2006 |

(Continued)

OTHER PUBLICATIONS

International Search Report for PCT/EP2016/050749, mailed May 23, 2016, 3 pages.

(Continued)

*Primary Examiner* — Jessica Worsham
(74) *Attorney, Agent, or Firm* — NIXON & VANDERHYE P.C.

(57) ABSTRACT

This invention relates to the use of the combination of 25-hydroxyvitamin D3 ("25-OH D3") and antioxidants/anti-inflammatories (ascorbic acid vitamin E and canthaxanthin) to make a premix or feed which can ameliorate various problems observed in poultry which have been subject to overfeeding. Feeds containing the 25-OH D3 and antioxidants/anti-inflammatories and premixes are also provided.

4 Claims, 3 Drawing Sheets

Related U.S. Application Data

(60) Provisional application No. 62/103,769, filed on Jan. 15, 2015.

(51) Int. Cl.

| | | |
|---|---|---|
| A61K 31/675 | (2006.01) | |
| A61K 33/04 | (2006.01) | |
| A61K 33/26 | (2006.01) | |
| A61K 33/32 | (2006.01) | |
| A61K 33/34 | (2006.01) | |
| A61P 3/06 | (2006.01) | |
| A61P 3/08 | (2006.01) | |
| A61P 9/00 | (2006.01) | |
| A61P 15/00 | (2006.01) | |
| A61P 15/08 | (2006.01) | |
| A61P 39/00 | (2006.01) | |

(56) References Cited

U.S. PATENT DOCUMENTS

| | | |
|---|---|---|
| 2006/0034912 A1 | 2/2006 | Giordano et al. |
| 2006/0069151 A1 | 3/2006 | Barella et al. |
| 2010/0098779 A1 | 4/2010 | Balzer et al. |
| 2010/0112162 A1 | 5/2010 | Tritsch et al. |
| 2013/0011377 A1 | 1/2013 | Perrin et al. |
| 2013/0281533 A1 | 10/2013 | Yamka et al. |

FOREIGN PATENT DOCUMENTS

| | | |
|---|---|---|
| CN | 102215700 | 10/2011 |
| JP | 48-67061 | 9/1973 |
| JP | 9-294544 | 11/1997 |
| JP | H11-35469 | 2/1999 |
| JP | 2005-519894 | 7/2005 |
| JP | 2006-510647 | 3/2006 |
| JP | 2008-106023 | 5/2008 |
| JP | 2009-27941 | 2/2009 |
| JP | 2011-511826 | 4/2011 |
| JP | 2011-511827 | 4/2011 |
| JP | 2012-509253 | 4/2012 |
| SU | 1748784 | 7/1992 |
| WO | 2008/031602 | 3/2008 |
| WO | 2010/057811 | 5/2010 |
| WO | 2014/102643 | 7/2014 |
| WO | 2014/191153 | 12/2014 |
| WO | 2014/202433 | 12/2014 |

OTHER PUBLICATIONS

About Dsm, "DSM Vitamin Supplementation Guidelines 2011 Health @Bullet Nutrition @Bullet Materials for domestic animals Guidelines for Optimum Vitamin Nutrition DSM vitamin supplementation guidelines are designed to provide Optimum Vitamin Nutrition under typical industry practices. Optimum Vitamin Nutrition co", Aug. 11, 2014, 14 pages.

R. L. Walzem et al., "Obesity-Induced Dysfunctions in Female Reproduction: Lessons from Birds and Mammals", Advances in Nutrition: An International Review Journal, vol. 5, No. 2, Mar. 1, 2014, pp. 199-206.

Amengual et al., "Beta-Carotene Reduces Body Adiposity of Mice via BCMO1", PloS One, vol. 6, No. 6, Jun. 1, 2011, 14 pages.

Bhuvaneswari et al., "Astaxanthin restricts weight gain, promotes insulin sensitivity and curtails fatty liver disease in mice fed an obesity-promoting diet", Process Biochemistry, vol. 45, No. 8, Aug. 1, 2010, pp. 1406-1414.

Buryakov et al., "Feeding of broiler chicks—involves addn. of sodium ascorbate to basic feed mix to increase live wt. gain", WPI / THOMSON, vol. 1993, No. 27, Jul. 23, 1992.

Muscogiuri et al., "Low Levels of 25(OH) D and insulin-resistance: 2 unrelated features or a cause-effect in PCOS?" Clinical Nutrition, vol. 31, No. 4, pp. 476-480.

Ruschkowski et al., Ionic and Endocrine Characteristics of Reproductive Failure in Calcium-Deficient and Vitamin D-Deficient Laying Hens, Poultry Science, vol. 71, Issue 10, pp. 1722-1732.

Stankiewicz et al., "Macro-elements composition of cystic and follicular fluid in the ovaries and their relationship to peripheral blood concentration in sows", Acta Veterinaria-Beograd, 65(2), 2015, pp. 217-225.

Vanga et al., "Role of Vitamin D in Cardiovascular Health", The American Journal of Cardiology, 2010, pp. 788-805.

Villar-Patiño et al., "Effects of Dietary Supplementation with Vitamin C or Vitamin E on Cardiac Lipid Peroxidation and Growth Performance in Broilers at Risk of Developing Ascites Syndrome", American Journal of Veterinary Research, American Veterinary Medicine Association, vol. 63, No. 5, May 1, 2002, pp. 673-676.

International Search Report for PCT/EP2016/050751 mailed Apr. 26, 2016, 3 pages.

International Search Report for PCT/EP2016/050753 mailed Apr. 20, 2016, 3 pages.

International Search Report for PCT/EP2016/050755 mailed Apr. 21, 2016, 3 pages.

International Search Report for PCT/EP2016/050759 mailed Apr. 26, 2016, 4 pages.

International Search Report for PCT/EP2015/050762 mailed Apr. 29, 2016, 5 pages.

International Search Report for PCT/EP2016/050764 mailed Apr. 19, 2016, 3 pages.

Office action for U.S. Appl. No. 15/541,852 mailed May 30, 2018 (12 pages).

Office action for U.S. Appl. No. 15/542,143 mailed Aug. 10, 2018 (14 pages).

Office action for U.S. Appl. No. 15/542,187 mailed Jul. 25, 2018 (14 pages).

Office action for U.S. Appl. No. 15/542,500 mailed Sep. 10, 2018 (16 pages).

Office action for U.S. Appl. No. 15/542,509 mailed Sep. 7, 2018 (16 pages).

Official Action, Colombia Appln. No. NC2017/0007058, Aug. 17, 2018 (English Translation).

Written Opinion of the ISA for PCT/EP2016/050749 mailed May 23, 2016, 8 pages.

Written Opinion of the ISA for PCT/EP2016/050751 mailed Apr. 26, 2016, 6 pages.

Written Opinion of the ISA for PCT/EP2016/050753 mailed Apr. 20, 2016, 6 pages.

Written Opinion of the ISA for PCT/EP2016/050755 mailed Apr. 21, 2016, 8 pages.

Written Opinion of the ISA for PCT/EP2016/050759 mailed Apr. 26, 2016, 8 pages.

Written Opinion of the ISA for PCT/EP2016/050762 mailed Apr. 29, 2016, 7 pages.

Written Opinion of the ISA for PCT/EP2016/050764 mailed Apr. 19, 2016, 8 pages.

Office Action issued in JP Appln. No. 2017-534244 dated Jul. 23, 2019 (w/ translation).

Franks, S. "Polycystic Ovary Syndrome" NEJM, 333 (13), 853-861 (Year: 1995).

Franks, S. "Adult polycystic ovary syndrome begins in childhood" *Best Practice & Research Clinical Endocrinology and Metabolism*, 16 (2), 263-272 (Year: 2002).

Garcia et al., "Use of Vitamin $D_3$ and Its Metabolites in Broiler Chicken Feed on Performance, Bone Parameters and Meat Quality" *Asian-Aust. J. Anim. Sci*, vol. 26, No. 3: 408-415 (Mar. 2013).

Lui et al., "A short-term supranutritional vitamin E supplementation alleviated respiratory alkalosis but did not reduce oxidative stress in head stressed pigs" *Asian-Ausralas J Anim Sci*, vol. 31, No. 2: 263-269 (Feb. 2018).

Nielsen et al., "Elimination of Ascorbic Acid After High-Dose Infusion in Prostate Cancer Patients: A Pharmacokinetic Evaluation" *Basic & Clinical Pharmacology & Toxicology*, vol. 116: 343-348 (2015).

*Nutrient Requirements of Poultry: Ninth Revised Edition*, The National Academics of Sciences Engineering Medicine, 176 pages (1994).

(56) References Cited

OTHER PUBLICATIONS

Quaranta et al., "The effects of 'supra-physiological' vitamin $B_{12}$ administration on temporary threshold shift" *International Journal of Audiology*, vol. 43: 162-165 (2004).
Rosenfield, R.L. et al. "Dysregulation of cytochrome P450c17α as the cause of polycystic ovarian syndrome" Fertility and Sterility 1990, 53 (5), 785-791 (Year: 1990).
Vollbracht et al., "Commentary: Supraphysiological vitamin B12 serum concentrations without supplementation: the pitfalls of interpretation" *QJM: An International Journal of Medicine*, vol. 0, No. 0: 1-2 (2019).
Witmer et al., "Direct spectrophotometric measurement of supra-physiological levels of ascorbate in plasma" *Redox Biology*, vol. 8: 298-304 (2016).
Office Action issued in JP Appln. No. P2017-530279 dated Sep. 3, 2019 (translation).
Office Action issued in U.S. Appl. No. 15/541,793 dated Mar. 25, 2019.
Office Action issued in U.S. Appl. No. 15/541,793 dated Sep. 17, 2019.
Office Action issued in U.S. Appl. No. 15/541,852 dated Dec. 27, 2018.
Office Action issued in U.S. Appl. No. 15/542,143 dated Mar. 8, 2019.
Office Action issued in U.S. Appl. No. 15/542,500 dated May 23, 2019.
Office Action issued in U.S. Appl. No. 15/542,187 dated May 13, 2019.
Office Action issued in U.S. Appl. No. 15/542,509 dated May 23, 2019.
Cheng et al., "The coupling of epidermal growth factor receptor down regulations and cell cycle arrest in growth suppression of ovarian cancer cells by 1α, 25-dihydroxyvitamin $D_3$," *Modern Oncology*, vol. 18, No. 2: 229-232 (Feb. 2010).
Madar et al., "Effect of vitamin $D_3$ supplementation on glycated hemoglobin (HbA1c) fructosamine, serum lipids, and body mass index: a randomized, double-blinded, placebo-controlled trial among healthy immigrants living in Norway" *BMJ Open Diabetes Research & Care*, vol. 2: e000026, pp. 1-8 (2014).
Yan et al., "Preliminary study on the relationship between vitamin D and polycystic ovary syndrome" *Prog Obstet Gynecol*, vol. 19, No. 11 (Nov. 2010)—(w/ Abstract).
Office Action issued in ID Appln. No. P00201704557 dated Mar. 9, 2020.
Office Action issued in CN Appln. No. 201680005767.0 dated Sep. 1, 2020 (w/ translation).
Office Action issued in CN Appln. No. 201680005795.2 dated Sep. 1, 2020 (w/ translation).
Zhao et al., "Serum Vitabmin D Levels and Related Studies in Obese Patients with Hyperlipidemia" *Journal of Chinese Practical Diagnosis and Therapy*, vol. 26, No. 12: 1231-1233 (Dec. 2012) (w/ partial translation).
Zhen et al. "Prevention and Treatment of Osteoporosis and Drug Use Options" *Chinese Metrology Publishing House*, 1st Edition, p. 68 (Nov. 2000).
Examination Report issued in IN Appln. No. 201717028664 dated Dec. 29, 2020.

* cited by examiner

COMBINATION OF 25-HYDROXYVITAMIN D AND ANTIOXIDANTS/ANTI-INFLAMMATORIES FOR POULTRY OVARIAN HEALTH

CROSS-REFERENCE TO RELATED APPLICATIONS

This application is a continuation of commonly owned U.S. application Ser. No. 15/542,091, filed Jul. 7, 2017, which in turn is the U.S. national phase application of International Application PCT/EP2016/050749, filed Jan. 15, 2016, which designated the U.S. which claims the benefit of U.S. Provisional Application No. 62/103,769, filed Jan. 15, 2015 and claims priority to European Patent Application No. 15166937.1, filed May 8, 2015, the entire contents of each of which are hereby incorporated by reference.

BRIEF DESCRIPTION OF THE INVENTION

This invention relates to the combination of 25-hydroxyvitamin D ("25-OH D3" and/or "25-OH D2") and antioxidants/anti-inflammatories (ascorbic acid, Vitamin E and canthaxanthin) for use in poultry feed to benefit ovarian health. This combination of nutritional supplements protects poultry against various adverse effects in the ovaries which are associated with hyperphagia such as increased ovarian degeneration and increased tumor formation. It also relates to feed and feed premixes containing the combination of 25-hydroxyvitamin D and the antioxidants/anti-inflammatories for use in protecting ovarian health.

BACKGROUND OF THE INVENTION

Reproductive efficiency and the incidence of pathogenic disorders are directly influenced by the extent of ovary development and nutrition in poultry. For example, the finely tuned reproductive system of the broiler breeder female requires ovary, oviduct, brain, liver and skeletal system to communicate among themselves under the influence of lighting in the production of hatching eggs. The hypothalamus, located within the brain, is directly stimulated by light energy at photostimulation. The mature (reproductively functional) hypothalamus then secretes luteinizing hormone releasing hormone (LHRH), which acts on anterior pituitary to stimulate the production of luteinizing hormone (LH) and follicle stimulating hormone (FSH). Both LH and FSH target the ovary and stimulate ovarian hormone production and early follicle development, respectively.

The ovary of an immature pullet has only small undifferentiated follicles invisible to the naked eye. These follicles, upon sexual maturity, increase in size to form an array of small follicles as well as a hierarchy of large follicles varying in size. The small follicles produce estrogen after hypothalamic maturation. The large yellow follicles are usually defined as being greater than 1 cm in diameter, and their numbers are directly influenced by lighting program, plane of nutrition and breeder age. Progesterone released from the largest follicle triggers the ovulation process. Mature follicles are capable of producing progesterone only a few hours prior to ovulation. The liver is a key organ in egg production as it is the site of lipogenesis, leading to formation of fatty acids and subsequently triglycerides that contribute to egg yolk formation, which is in turn driven by estrogen. The skeletal system is intimately associated with egg production for its role in mobilizing, storing and releasing calcium under the influence of estrogen.

Hyperphagia and therefore adiposity occurs in broiler breeder females as a consequence of genetic selection for rapid growth in broiler chickens. Overfeeding-induced ovarian dysfunction and reproductive inefficiency as well as metabolic disorders like ascites, sudden death syndrome and fatty liver in broiler breeder females is a consequence of lipotoxicity development as result of fuel overloading the biological system. Therefore, the challenge of managing modern female broiler breeder strains is the inability of these hens to adequately self-regulate feed intake during growth and development to achieve an optimal body weight and composition to support efficient egg and chick production. As such, broiler breeder females are subject to a high degree of restricted feeding regimen. The primary mechanism in which feed restriction benefits reproductive efficiency in broiler breeder females is the control of follicle development or rather limiting the formation of excessive numbers of ovarian yellow follicles arranged in multiple hierarchies.

Broiler breeder females overfed during reproductive development not only produce excess large yellow ovarian follicles but also generate a greater number of atretic yellow follicles and commonly display erratic oviposition and defective egg syndrome (EODES) that include several reproductive problems such as follicular atresia, the production of soft-shelled or membranous eggs, double-yolked eggs, egg yolk peritonitis (presence of egg yolk in the abdominal cavity), multiple egg days and oviposition not occurring in sequence, resulting in increased production of unsettable eggs.

Controlled studies reported that voluntary feeding (i.e., broiler breeder hens to satiation) resulted in poor egg production, high rate of mortality and abnormal ovarian structure (mainly overt hierarchical follicle atresia). Lipotoxicity results in impaired ovarian dysfunctions, including follicle atresia, ovarian regression, and a decline of circulating estradiol levels in feed-satiated hens.

Despite restricted feeding regimen strictly implemented in commercial broiler breeder flocks, it is still very easy to overfeed breeder hens due to their intrinsic hyperphagia. Furthermore, breeder farm managers are confronted as to when and how to feed before and during the start of egg production as well as towards, during and after peak production. The basic fundamental question to ask what and how management and nutritional tools breeder farm managers can apply and implement to ameliorate the adverse and deleterious effects of reproductive efficiency associated with obesity in overweight hens.

Hy•D® (registered trademark for 25-OH-D3; available from DSM Nutritional Products, Switzerland has been used to promote bone health in poultry.

The combination of 25-OH D3 and canthaxanthin has also been used in poultry. WO2010/057811 (DSM IP ASSETS, BV) describes the combination for use in improving hatchability, fertility, and lower embryo mortality in poultry. The combination is commercially available under the trademark MAXICHICK. There is no mention in the patent publication of the inclusion of ascorbic acid, the use of high vitamin E levels, nor the uses to benefit ovarian health.

Vitamin C (ascorbic acid) is often not included as a supplement in poultry diets, as chicken, under normal rearing conditions can produce sufficient Vitamin C. However, it has been used in some specific conditions, such as in heat stress situations.

Vitamin E is generally added to poultry feed. Recommended doses for broilers tends to range from about 50-100 IU/kg feed, depending on the age of the animal.

WO14/202433 (DSM IP ASSETS B.V) teaches the combination of canthaxanthin and 25-OH D3 to improve internal egg quality, i.e. enhancing the strength of vitelline membrane that envelopes the yolk. There is no teaching to add ascorbic acid to the combination, nor for its use in ameliorating the adverse effects of hyperphagia-related obesity.

WO14/191153 (DSM IP ASSETS B.V) teaches the combination of canthaxanthin and at least one of Vitamin C, Vitamin E, selenium, and optionally at least one of thymol, eugenol, vanillin and gamma-terpinene can improve immune statues, bone health, skeletal development and growth and feed conversion, particularly when flocks are subject to stress associated with vaccination.

Thus there is a need to reduce or ameliorate the metabolic and hormonal dysregulations as a result of hyperphagia in broiler breeder hens which induce affect ovarian health.

DETAILED DESCRIPTION OF THE INVENTION

It has been found, accordance with this invention that the combination of 25-hydroxyvitamin D (25-OH D3 and/or 25-OH D2) and antioxidants/anti-inflammatories ameliorates adverse ovarian health observed when poultry is fed ad libitum or experiences hyperphagia-related obesity. The antioxidants of this invention comprise the combination of ascorbic acid, vitamin E and canthaxanthin, although it has also been found, in accordance with this invention that they antioxidants also possess anti-inflammatory activities and thus are referred to as "antioxidant/anti-inflammatories".

Thus one aspect of this invention is the combination of 25-OH D3, canthaxanthin, vitamin E and ascorbic acid to benefit ovarian health. Another embodiment is the combination of 25-OHD2, canthaxanthin, Vitamin E and ascorbic acid to benefit ovarian health. Another embodiment is the combination of 25-OHD3, 25-OHD2, canthaxanthin, Vitamin E and ascorbic acid to benefit ovarian health.

As 25-OH D2 and 25-OH D3 may act in a similar fashion after administration, it is envisioned that either may be used separately in combination with antioxidants/anti-inflammatories/anti-inflammatories, or a mixture of both 25-OH D3 and 25-OH D2 may be used in combination with antioxidants/anti-inflammatories/anti-inflammatories. If used together, the ratio of 25-OH D3:25-OH D3 is not a critical part of the invention.

Another aspect of this invention is the combination of 25-OH D, canthaxanthin, vitamin E and ascorbic acid, which optionally further comprises at least one further bio-active ingredient selected from the group consisting of:
Vitamin D, Vitamin B2, Vitamin B6, Niacin, Zinc, Copper, Manganese, and Selenium. Preferably the 25-OH D is 25-OH D3 to benefit ovarian health. Preferably at least Vitamin D is a further bio-active ingredient. Sometimes the further bio-active ingredients include at least Vitamin D and Selenium. In some cases, all the further bio-active ingredients are added.

A further aspect is the combination of 25-OH D, canthaxanthin, vitamin E and ascorbic acid which optionally further comprises at least one further bio-active ingredient selected from the group consisting of Vitamin D, Vitamin B2, Vitamin B6, Niacin, Pantothenic Acid, Folic Acid, Biotin, Zinc, Copper, Manganese, Selenium, and combinations thereof to benefit ovarian health. Preferably the 25-OH D is 25-OH D3. Sometimes, the further bio-active ingredient includes biotin. Sometimes the further bio-active ingredient includes Vitamin D and biotin. Sometimes the further bio-active ingredient includes all the aforementioned optionally bio-active ingredients.

Another aspect of this invention is a poultry feed which benefits ovarian health comprising the combination of 25-OH D2 or 25-OH D3 or mixtures thereof, ascorbic acid, Vitamin E and canthaxanthin.

Yet another embodiment is poultry feed which benefits ovarian health comprising the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Zinc, Copper, Manganese, Selenium and combinations thereof. Preferably the 25-OH D is 25-OH D3. Sometimes the further bio-active ingredients include at least Vitamin D and Selenium. In some cases, all the further bio-active ingredients are added.

Another embodiment is poultry feed benefitting ovarian health comprising the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof. Sometimes, the further bio-active ingredient includes biotin. Preferably the 25-OH D is 25-OH D3. Sometimes the further bio-active ingredient includes Vitamin D and biotin. Sometimes the further bio-active ingredient includes all the aforementioned optionally bio-active ingredients.

Another aspect of this invention are premixes for poultry feed that benefits ovarian health which comprise the combination of 25-OH D, vitamin E, ascorbic acid and canthaxanthin. Preferably, the 25-OH D is 25-OH D3. In some embodiments the feed and premix also comprises at least one further bio-active ingredient selected from the group consisting of:
Vitamin D, Vitamin B2, Vitamin B6, Niacin, Zinc, Copper, Manganese, Selenium and combinations thereof. Sometimes the further bio-active ingredients include at least Vitamin D and Selenium. In some cases, all the further bio-active ingredients are added.

Another aspect of this invention are premixes for poultry feed which benefits ovarian health which further comprise at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof. Sometimes, the further bio-active ingredient includes biotin. Sometimes the further bio-active ingredient includes Vitamin D and biotin. Sometimes the further bio-active ingredient includes all the aforementioned optionally bio-active ingredients.

In another aspect, the 25-OH D and antioxidants/anti-inflammatories of this invention are all used in poultry which are fed a complete diet, so they are not vitamin/mineral deficient. Thus, the 25-OH D and antioxidant/combination of this invention is not acting to remedy a vitamin or other nutrient deficiency. It can be considered a supra-physiological dosage.

When using the poultry feed of this invention, the animals may be fed ad libitum and the ill effects on ovarian health normally experienced will be experienced to a lesser degree or not at all. This results in easier flock management, and eliminates the problems encountered where the flock is fed a restricted diet, but certain individual birds still exhibit hyperphagia, and may show aggressive behaviors towards other birds.

BRIEF DESCRIPTION OF THE FIGURES

FIG. 1, top left shows an abnormal ventricle, as seen in the untreated group, as compared to a normal ventricle. The middle left and right show transudate within the pericardium. The lower row shows normal pericardia.

FIG. 2 shows ascites which were found in the abdominal cavity (top left) versus a normal abdominal cavity. The lower row shows tumor-like morphology in the ovary (left), degenerate morphology (center) and normal morphology (right).

FIG. 3 shows abnormal livers (cirrhosis, left) (fatty liver, center) and a normal liver (right).

Figure 1:
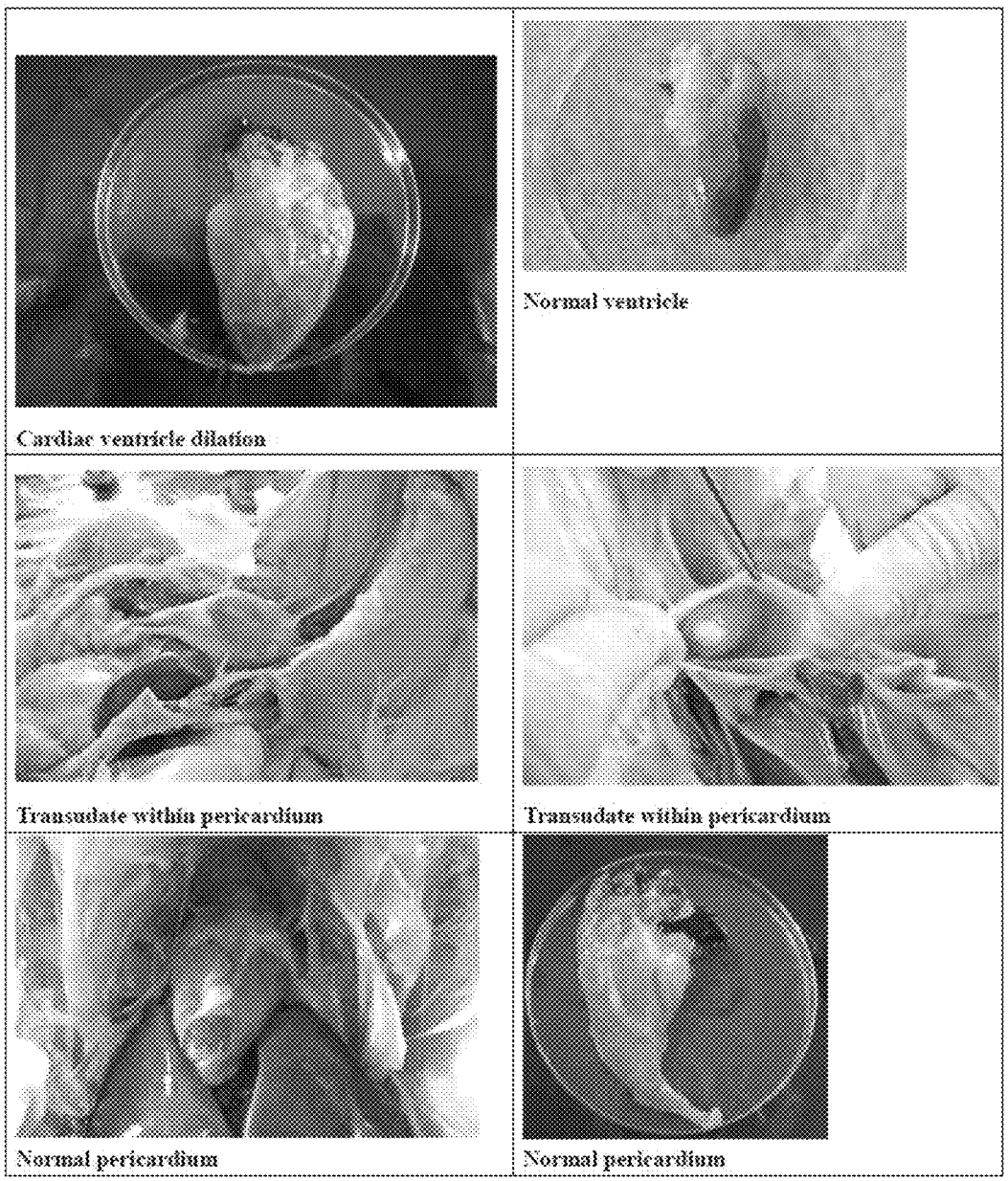
FIGS. 1-3 show pictures taken during the necropsy of broiler hens in response to ad libitum feed intake in combination with vitamin D and antioxidant inclusion. Hens were necropsied after 10 weeks of the feeding trial.
Figure 2:
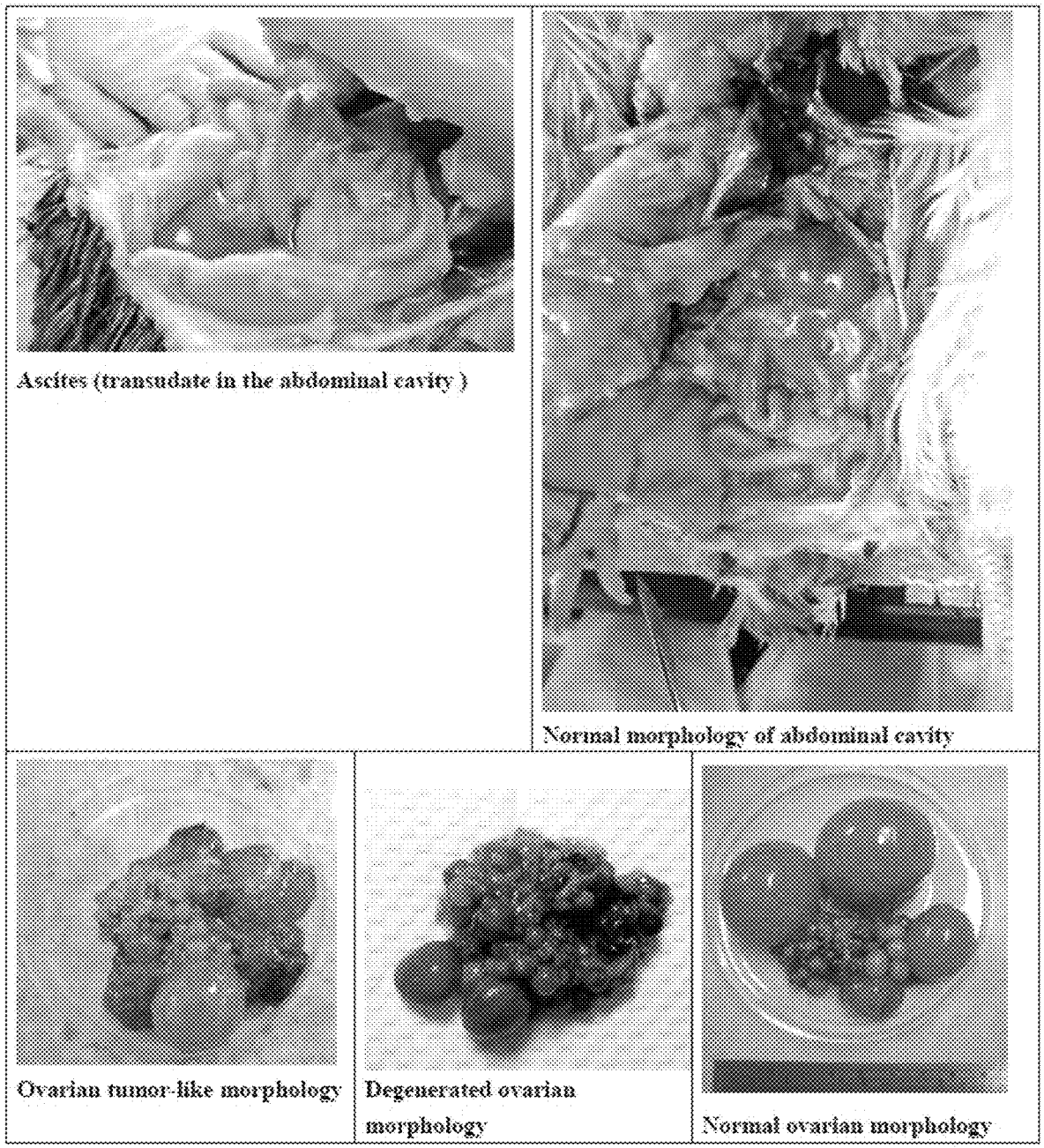
Figure 3:
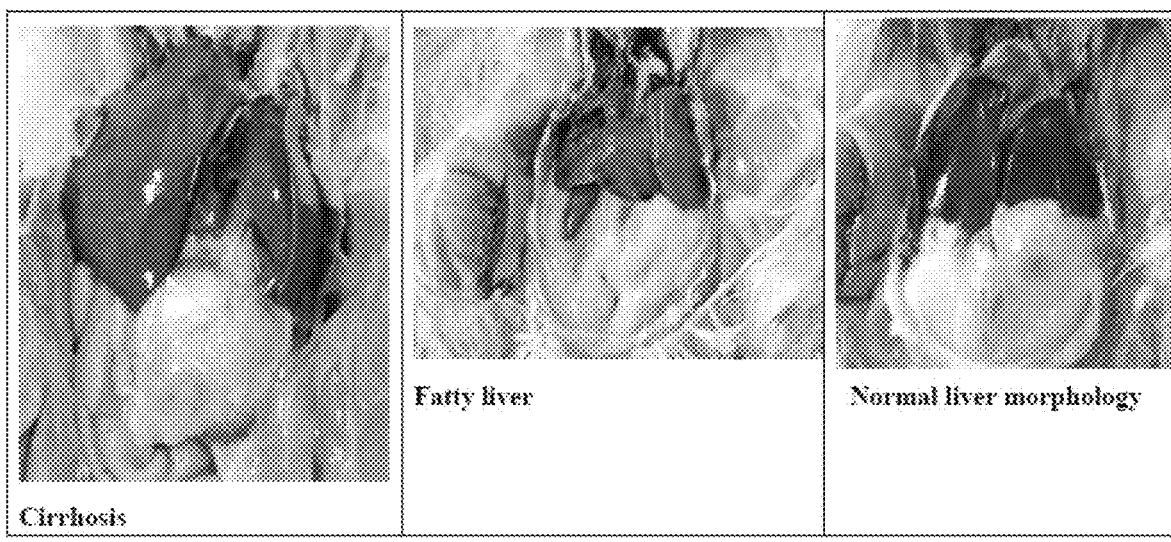

As used throughout this specification and claims, the following definitions apply:

"25-OH D" refers to any form of 25-hydroxyvitamin D (i.e. either 25-OH D2 or 25-OH D3, or mixes thereof). 25-OH D3 specifically refers to 25-hydroxyvitamin D3; 25-OH D2 specifically refers to 25-hydroxyvitamin D2.

"Poultry" means any domesticated fowl, including chickens (including broiler, layers and breeding hens), ducks, geese, turkeys, quail, and ostriches.

"Hyperphagia" is excessive eating; the animal does not voluntarily limit its feeding.

"Ovarian health" in this invention relies on the following distinct measurable parameters: the amount of ovarian degeneration and ovarian tumors. Benefitting/improving ovarian health thus means that at least one of the following conditions is present upon feeding the combination of this invention:

a) ovarian degeneration is lessened, occurs at a later onset, or does not occur b) ovarian tumors are reduced in number, reduced in size, reduced in both size and number, occur at a later onset, or do not occur.

"Ascorbic Acid" and "Vitamin C" are used interchangeably throughout the specification and claims.

It has been found in accordance with this invention, that the use of feed comprising 25-OH D3, vitamin E, canthaxanthin and ascorbic acid can specifically contribute to ovarian health. Broiler breeder females overfed during reproductive development not only produce excess large yellow ovarian follicles but also generate a greater number of atretic yellow follicles and commonly display erratic oviposition and defective egg syndrome (EODES) that include several reproductive problems such as follicular atresia, the production of soft-shelled or membranous eggs, double-yolked eggs, egg yolk peritonitis (presence of egg yolk in the abdominal cavity), multiple egg days and oviposition not occurring in sequence, resulting in increased production of unsettable eggs. Use of the feed/premix of this invention can lessen, reduce, ameliorate or eliminate each of these conditions.

Thus one aspect of this invention is a combination comprising 25-Hydroxy vitamin D, ascorbic acid, Vitamin E and canthaxanthin for use in a poultry feed promoting ovarian health, wherein ovarian health is indicated by at least one indicia of ovarian health selected from the group consisting of:

a) reduced ovarian degeneration, occurrence of ovarian degeneration at a later onset, or no occurrence of ovarian degeneration; and b) reduction in the amount of ovarian tumors, reduction in size of ovarian tumors, reduction in both size and number of ovarian tumors, occurrence at a later onset, or no occurrence of ovarian tumors.

Specifically it has been found that feed comprising 25-OH D3, vitamin E, canthaxanthin and ascorbic acid can be used in an ad libitum feeding scheme, and will result in poultry which exhibit at least one of these characteristics:

a) ovarian degeneration is lessened, occurs at a later onset, or does not occur;

b) ovarian tumors are reduced in number, reduced in size, reduced in both size and number, occur at a later onset, or do not occur.

Hens with ovarian degeneration, large follicle atresia or tumors or other abnormal morphology such as internal ovulation, tend to have a lower egg production rate than in their past records. Hens with obesity and related dysregulations such as plasma lipids and ceramide or insulin and leptin level, or tissue cytokine and lipid content tend to have a rapid ovarian degeneration and other abnormalities and thereby a lower egg production rate which can be easily monitored.

Doses

25-OH D3: The amount of 25-OH D3 can range from 15-200 µg/kg feed. Preferably, the amount of 25-OH D3 is from 35-150 µg/kg feed. For feed with a low dose of the combination of the invention, 35 µg per kg 25-OH D3/feed is preferred; for food with a medium dose of the combination, 69 µg per kg feed is preferred; and for food with a high dose of 150 µg feed is preferred.

Vitamin E: The amount of Vitamin E can range from 40-400 mg/kg feed. Preferably the amount is 80-300 mg/kg feed. For feed with a low dose of the combination of the invention, 80 mg/kg Vitamin E is preferred. For feed with a medium dose, 150 mg Vitamin E is preferred; for feed with a high dose, 300 mg/kg Vitamin E is preferred.

Canthaxanthin: The amount of canthaxanthin can range from 1-15 mg/kg feed. Preferably the amount is 3-12 mg/kg feed. For feed with a low dose of the combination of the invention, 3 mg/kg canthaxanthin is preferred. For feed with a medium dose, 6 mg canthaxanthin is preferred; for feed with a high dose, 12 mg/kg canthaxanthin is preferred.

Ascorbic Acid: The amount of ascorbic acid can range from 40-400 mg/kg feed. Preferably the amount is 100-300 mg feed. For feed with a low dose of the combination of the invention, 100 mg/kg ascorbic acid is preferred. For feed with a medium dose, 150 mg ascorbic acid is preferred; for feed with a high dose, 300 mg/kg ascorbic acid is preferred.

Thus specific preferred feeds of this invention comprise the following dosages (all amounts are per kg/feed):

Preferred Feed #1:

25-OH D3: 15-200 µg,

Vitamin E: 40-400 mg,

Canthaxanthin: 1-15 mg; and

Ascorbic acid: 40-400 mg.

Preferred Feed #2:

25-OH D3: 35-150 µg,

Vitamin E: 80-300 mg,

Canthaxanthin: 3-12 mg, and

Ascorbic acid: 80-300 mg

Preferred Feed #3: (Low dose feed) This feed is preferred for mildly obese poultry.
  25-OH D3: 35 μg
  Vitamin E: 80 mg
  Canthaxanthin: 3 mg
  Ascorbic acid: 80 mg.
Preferred Feed #4 (medium dose feed) This feed is preferred for moderately to severely obese poultry:
  25-OH D3: 69 μg
  Vitamin E: 150 mg
  Canthaxanthin: 6 mg
  Ascorbic acid: 150 mg.
Preferred Feed #5 (high dose feed) This feed is preferred for severely obese poultry:
  25-OH D3: 150 μg
  Vitamin E: 300 mg
  Canthaxanthin: 12 mg
  Ascorbic acid: 300 mg.
Optional Additional Ingredients
  To each of the feeds listed above, at least one of the additional ingredients may be added. Preferably at least one, and more preferably more than one of the following ingredients are added. In other embodiments, all the following ingredients are added:
  Vitamin D3—generally this is present in poultry diets at approximately 2500 IU per kg feed. In accordance with this invention, if desired, the amount of Vitamin D is increased to at least 3000 IU per kg.
  Vitamin B2: this can be added at 3-25 mg per kg; preferably from 6-20 mg/kg. For low dose feed, 6 mg/kg is preferred. For medium dose feed, 14 mg/kg is preferred; and for high dose feed 20 mg/kg is preferred.
  Niacin: this can be added at 25-300 mg per kg feed. Preferably it ranges from 60-200 mg/kg. For low dose feed, 60 mg/kg is preferred. For medium dose feed, 120 mg/kg is preferred; and for high dose feed 200 mg/kg is preferred.
  Pantothenic acid: this can be added at 10-120 mg per kg feed. Preferably it ranges from 15-80 mg/kg. For low dose feed, 15 mg/kg is preferred. For medium dose feed, 30 mg/kg is preferred; and for high dose feed 80 mg/kg is preferred.
  Folic acid: this can be added at 1-8 mg per kg feed. Preferably it ranges from 2-6 mg/kg. For low dose feed, 2 mg/kg is preferred. For medium dose feed, 4 mg/kg is preferred; and for high dose feed 6 mg/kg is preferred.
  Biotin: this can be added at 0.05-1.0 mg/kg feed. Preferably it ranges from 0.2-0.8 mg/kg. For low dose feed, 0.2 mg/kg is preferred. For medium dose feed, 0.4 mg/kg is preferred; and for high dose feed 0.8 mg/kg is preferred.
  Zinc: this can be added at 50-300 mg/kg feed. Preferably it ranges from 70-250 mg/kg. For low dose feed, 70 mg/kg is preferred. For medium dose feed, 125 mg/kg is preferred; and for high dose feed 250 mg/kg is preferred.
  Copper: this can be added at 5-50 mg/kg feed. Preferably it ranges from 10-30 mg/kg. For low dose feed, 10 mg/kg is preferred. For medium dose feed, 20 mg/kg is preferred; and for high dose feed 30 mg/kg is preferred.
  Manganese: this can be added at 50-300 mg/feed. Preferably it ranges from 80-270 mg/kg. For low dose feed, 80 mg/kg is preferred. For medium dose feed, 150 mg/kg is preferred; and for high dose feed 270 mg/kg is preferred.
  Selenium: this can be added at 0.05-0.6 mg/kg feed. Preferably it ranges from 0.1-0.4 mg/kg. For low dose feed, 0.1 mg/kg is preferred. For medium dose feed, 0.2 mg/kg is preferred; and for high dose feed 0.4 mg/kg is preferred.

The following non-limiting Examples are presented to better illustrate the invention.

EXAMPLES

Example 1

Materials and Methods

A total of thirty 45-week-old broiler breeder hens (ROSS 308) were obtained from a commercial flock for the study. A basal broiler breeder laying diet was formulated as shown in Table 1. The calculated nutrient composition is shown in Table 2.

TABLE 1

Ingredient composition of the basal broiler breeder laying diets.

| Composition | %, w/w |
|---|---|
| Corn | 66.9 |
| Soybean meal | 22.2 |
| Oil fat | 1.67 |
| Ca Carbonate (ground oyster shell) | 6.36 |
| Dicalcium phosphate | 1.8 |
| Choline-Cl (70%) | 0.1 |
| Mineral Premix[1] | 0.1 |
| Copper sulfate | 0.05 |
| Vitamin Premix[2] | 0.1 |

[1]Mineral premix provided (per kg of diet for treatment groups 1, 2 and 3): Cu 18 mg; I 1.1 mg; Fe 80 mg; Mn 150 mg; Zn 125 mg; and Se 0.25 mg.
[2]Refer to Table 2 for further detail.

TABLE 2

Vitamin premix composition (provided per kg of diet)

| Vitamin | Treatments 1 and 2<br>1 = restricted feeding<br>2 = ad libitum feeding | Treatment 3<br>3 = ad libitum feeding +<br>25-OH-D3 +<br>antioxidants/anti- |
|---|---|---|
| A (IU) | 10000 | 12000 |
| D3 (IU) | 2500 | 3000 |
| E (mg) | 100 | 150 |
| K3 (mg) | 3 | 5 |
| B1 (mg) | 3 | 3 |
| B2 (mg) | 8 | 14 |
| B6 (mg) | 6 | 8 |
| B12 (mg) | 0.03 | 0.03 |
| Niacin (mg) | 60 | 120 |
| Pantothenic acid (mg) | 18 | 30 |
| Folic acid (mg) | 1 | 4 |
| Biotin (mg) | 0.2 | 0.4 |
| C (ascorbic acid) (mg) | 0 | 150 |
| 25-OH-D3 (mcg) | 0 | 69 |
| Canthaxanthin (mg) | 0 | 6 |

TABLE 3

Calculated nutrient composition (%) of the basal broiler breeder laying diets.

| Composition | % w/w |
|---|---|
| Crude protein | 16 |
| Crude fat | 4.2 |
| Calcium | 3.1 |

TABLE 3-continued

| Calculated nutrient composition (%) of the basal broiler breeder laying diets. | |
|---|---|
| Composition | % w/w |
| Sodium | 0.16 |
| Total Phosphorus | 0.64 |
| Total ME | 2910 kcal/kg |

Diet was supplemented with or without 25-OH D3 at 69 mcg/kg diet in combination with antioxidants/anti-inflammatories (ascorbic acid, canthaxanthin) and enriched levels of selected vitamins. Hens were randomly allocated to 3 treatment groups according to feeding regimen (restricted and ad libitum) as follows:

1. Basal diet—restricted feeding (140 g/day)
2. Basal diet—ad libitum feeding
3. Basal diet—ad libitum feeding+25-OH-D3 at 69 mcg/kg diet+antioxidants/anti-inflammatories They were individually-housed in wire cages placed in a controlled room with 14 h:10 h light:dark period and at a temperature of 25±3° C. Water was available ad libitum. The experimental period was lasted for 10 weeks. Three weeks after the feeding trial, some birds were used for relevant plasma parameter analyses. At the end of experiment, hens were euthanized and sacrificed for tissue sample collection for further studies.

Results and Discussion

25-Hydroxy D3 and Antioxidants/Anti-Inflammatories Lowered Mortality and Improved Egg Production, Ovarian Morphology and Plasma 1713 Estradiol Level Secretion of estradiol is the hallmark of successful ovulatory follicles. In addition to its role in triggering the preovulatory surge of gonadotropins, estradiol is an important intra-ovarian growth, differentiation, and survival factor. Inclusion of 25-hydroxy D3 and antioxidants/anti-inflammatories reduced mortality and incidence of ovarian degeneration and ovarian-tumor-like morphology, increased egg production and sustained plasma estradiol levels in birds under ad libitum feed intake.

In the group of hens fed the 25-OH D3+antioxidant diet, a lower number of deaths was observed compared to those fed the non-supplemented diet ad libitum. Egg production was significantly higher, and the incident of degenerated ovaries and the incidence of ovarian tumors was lower in the group fed 25-OH D3+anti-oxidants compared to those fed ad-libitum.

CONCLUSIONS

Supplemental 25-hydroxy D3 and antioxidants/anti-inflammatories ameliorated deleterious effects associated with overfeeding of broiler breeder females by lowering mortality rate and improving ovary function and therefore reproductive performance of overfed broiler breeder hens.

The invention claimed is:

1. A method of promoting ovarian health in poultry, wherein ovarian health is indicated by at least one indicia of ovarian health selected from the group consisting of reduced ovarian degeneration, occurrence of ovarian degeneration at a later onset, or no occurrence of ovarian degeneration; reduction in the amount of ovarian tumors, reduction in size of ovarian tumors, reduction in both size and number of ovarian tumors, occurrence of ovarian tumors at a later onset, and no occurrence of ovarian tumors; wherein the method comprises feeding poultry a feed comprising a premix, wherein the premix consists of:
   (i) 15-200 µg/kg feed of 25-Hydroxy vitamin D3 (25-OH D3),
   (ii) 40-400 mg/kg feed of ascorbic acid,
   (iii) 40-400 mg/kg feed of Vitamin E, and
   (iv) 1-15 mg/kg feed of canthaxanthin.

2. The method according to claim 1, wherein the step of feeding poultry is practiced ad libitum.

3. The method according to claim 2, wherein the premix further consists of at least one further bio-active ingredient selected from the group consisting of Vitamin D, Vitamin B2, Vitamin B6, Niacin, Zinc, Copper, Manganese, and Selenium.

4. The method according to claim 1, wherein the premix further consists of at least one further bio-active ingredient selected from the group consisting of Vitamin D, Vitamin B2, Vitamin B6, Niacin, Zinc, Copper, Manganese, and Selenium.

* * * * *